United States Patent [19]

Hung et al.

[11] Patent Number: 6,028,165

[45] Date of Patent: Feb. 22, 2000

[54] EPOXIDES CONTAINING A PERFLUOROVINYL GROUP

[75] Inventors: Ming-Hong Hung, Wilmington, Del.; Shlomo Rozen, Tel Aviv, Israel

[73] Assignee: E. I. du Pont de Nemours and Company, Wilmington, Del.

[21] Appl. No.: 09/277,939

[22] Filed: Mar. 29, 1999

Related U.S. Application Data

[62] Division of application No. 08/243,428, May 16, 1994, Pat. No. 5,914,412.

[51] Int. Cl.$^7$ .............................. C08G 59/00; C08G 65/00
[52] U.S. Cl. ........................... 528/403; 528/401; 525/199; 526/247
[58] Field of Search .................................... 528/403, 401; 525/199; 526/247

[56] References Cited

U.S. PATENT DOCUMENTS

| | | | |
|---|---|---|---|
| 4,544,720 | 10/1985 | Ohmori et al. | 526/247 |
| 4,581,412 | 4/1986 | Ohmori et al. | 525/199 |
| 5,015,790 | 5/1991 | Hung | 570/125 |
| 5,043,490 | 8/1991 | Hung et al. | 570/136 |

FOREIGN PATENT DOCUMENTS

| | | | |
|---|---|---|---|
| 782615 | 9/1957 | United Kingdom | 549/563 |

OTHER PUBLICATIONS

W. Sheppard et al., Organic Fluorine Chemistry, p. 189–191, W. A. Benjamin, Inc., New York 1969.
C. Walling et al., Organic Reactions, vol. 13, p. 130–131, John Wiley & Sons, New York 1963.
J. Roberts et al., Basic Principles of Organic Chemistry, p. 386 and 421, W. A. Benjamin, Inc. New York 1964.
S. Rozen et al., Angew. Chem. Int. Ed. Eng., Epoxidation of Olefins with Chemical Fluorine in Water/Acitonitrile, p. 564–585, Mixtures 25 (6).

*Primary Examiner*—Duc Truong

[57] ABSTRACT

Epoxides containing a perfluorovinyl group, and polymers made therefrom by polymerization of the epoxy function are disclosed. Such epoxides form polymers and copolymers useful for coatings, adhesion control agents, surface modifiers and crosslinking agents.

10 Claims, No Drawings

EPOXIDES CONTAINING A PERFLUOROVINYL GROUP

This is a division of application Ser. No. 08/243,428 filed May 16, 1994, now U.S. Pat. No. 5,914,412.

FIELD OF INVENTION

Epoxides containing a perfluorovinyl group, and polymers made therefrom by polymerization of the epoxy group, are provided.

BACKGROUND OF THE INVENTION

U.S. Pat. Nos. 4,544,720 and 4,581,412 disclose compounds of the formula $CF_2=Cr-(-CF_2-)-_m-(-CH_2-)-_nX$, wherein m is 0 or an integer of 1–10, n is 0 or an integer of 1–4, and (most pertinently) X is

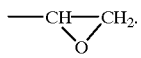

In the case where m is 0 and n is 2, 3 or 4, these disclosed compounds are identical to those described in this application. The only example in these patents of these compounds made is where m is 0 and n is 1. The chemistry described for this synthesis in the specification of these patents (in '720 at col. 3, lines 55 to end; in '412 at col. 3, line 61 to col. 4, line 8), uses the addition of allyl alcohol to a perhalogenated-alkyl iodide, which will only produce the compound where n is 1. Chemistry is described (in '720 at col. 3, lines 43–49; in '412 at col. 3, lines 36–44), but not done, for the preparation of other epoxides, including those described in this application. However, the preparation of the starting material for that synthesis is neither described nor is a reference given. Therefore, although the instant compounds are mentioned, ore of ordinary skill in the art would not be able to make them from disclosures in these patents.

It is the object of this invention to provide epoxides containing a perfluorovinyl group, may be polymerized through either the vinyl group (see U.S. Pat. Nos. 4,544,720 and 4,581,412) or through the epoxy group (infra). It is a further object of this invention to provide polymers and copolymers made from these epoxide compounds by polymerization of the epoxy group.

SUMMARY OF THE INVENTION

Epoxides containing a perfluorovinyl group, and polymers made therefrom by polymerization of the epoxy function are disclosed. The epoxides are of the formula

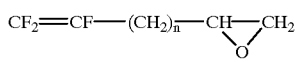

wherein n is an integer of 2 through 10.

Such epoxides may be polymerized through either the epoxy or vinyl functionality to form polymers useful for coatings, adhesion control agents, surface modifiers and crosslinking agents. Polymers of the structure

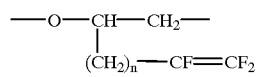

wherein n is an integer from 2 through 10 are also disclosed.

DETAILS OF THE INVENTION

This invention concerns a compound of the formula

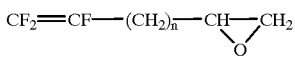

wherein n is an integer of 2 through 10.

In these compounds, herein sometimes termed epoxides containing a perfluorovinyl group, it is preferred if n is 2, 4 or 6.

The epoxides are made by the selective epoxidation of the corresponding diene, using a combination of fluorine, water and acetonitrile. Such procedures are found in S. Rozen and M. Brand, Angew. Chem. Int. Ed., vol. 25, pp. 554–555 (1986) and commonly assigned U.S. patent application Ser. No. 420,454, filed Oct. 12, 1989, both of which are hereby included by reference. Further illustration of the epoxidation is found in the Examples.

The dienes that are epoxidized can be made by methods found in commonly assigned U.S. patent applications Ser. No. 450,257, filed Dec. 13, 1989, and 530,638, now U.S. Pat. Nos. 5,015,790 and 5,043,490 repectively, the latter of which is filed herewith, and both of which are included herein by reference. Specific illustrations will be found in the Examples.

The epoxides containing a perfluorovinyl group are useful as monomers, see below and U.S. Pat. Nos. 4,544,720 and 4,581,412.

Also contemplated by this invention are a polymer, comprising, units of the formula

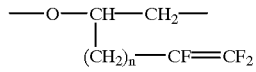

wherein n is an integer from 2 through 10.

In preferred polymers n is 2, 4 or 6, and in especially preferred polymers, n is 4. It is also preferred if the polymer consists essentially of the units

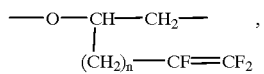

in other words is a homocolymer.

In another preferred embodiment it is preferred if the polymer further comprises units of the formula $-O-CH_2-CH_2-$ and/or units of the formula

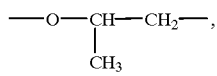

in other words, copolymers with ethylene oxide and/or propylene oxide, respectively. By the term homopolymer above is meant that only one or more epoxides containing a perfluorovinyl group are used as monomers to make the homopolymer. Homopolymers and copolymers mav include variations such as head to head, tail to tail and head to tail sequences.

Polymers from these monomers have been made (see U.S. Pat. Nos. 4,544,720 and 4,581,412), but these polymers have been made by polyme-ization of the vinyl group. The instant polymers can be made by an acid catalyzed polymerization of the epoxy group, see for example British Patent 782,615, which is hereby included by reference, for typical procedures. Specific polymerizations are illustrated in the Examples.

It has been found that compounds wherein n=4 polymerize exceptionally easily, and the monomeric epoxide containing a fluorovinyl group must be stored at about 0° C. or less to prevent polymerization. Note in Example 4 that the polymerization is done thermally in the absence of catalyst.

EXPERIMENTAL PROCEDURES

General Procedure for Working with Fluorine

Fluorine is a strong oxidizer and a very corrosive material. An appropriate vacuum line made from copper or Monel® in a well ventilated area should be constructed for working with this element. The reactions themselyes can be carried out in glass vessels. If elementary precautions are taken, work with fluorine is relatively simple.

General Procedure for Producing the Oxidizing Reaent

Mixtures of 10%–15% $F_2$ diluted with nitrogen are used in this work. The gas mixtures are prepared in a secondary container before the reaction is started. This mixture is then passed in a rate of about 400 ml per minute through a cold (−10° C.) and vigorously stirred mixture of 400 ml $CH_3CN$ and 40 ml $H_2O$. The formation of the oxidizing power is monitored by reacting aliquots with acidic aqueous solution of KI. The liberated iodine is then titrated with thiosulfate. Concentrations of more then a mol/liter oxidizing reagent can be reached.

General Epoxidation Procedure

An appropriate amount of olefin (see discussion) is dissolyed in about 50 ml of $CH_2Cl_2$ cooled to 0° C. and added in one portion to the reaction vessel in which the oxidizing agent has been preared. The temperature and the time of the reaction depends on the individual olefin. After the reaction is completed, the reaction mixture is neutralized with saturated sodium bicarbonate solution. The reaction mixture is then poured into 1.5 liter of water, extracted with $CFCl_3$ and washed with $NaHCO_3$ and water until neutral. The organic layer is dried over $MgSO_4$, and the solyent distilled under reduced pressure, preferably at room temperature. The crude product is usually distilled under reduced pressure.

EXAMPLE 1

Epoxidation of 1,1,2-Trifluoro-1,5-Hexadiene 200 mmols of the oxidizing solution were made. To this solution 9.5 g (70 mmol) of the olefin dissolved in 30 ml $CH_2Cl_2$ were added. After 2 minutes at 0° C. the reaction was worked up as described above. After the distillation of the solvent the reaction mixture was distilled and the main fraction which was identified as 5,6-epoxy-1,1,2-trifluoro-1-hexene with a bp=58° C./30 mm, yield 60%; IR=1200, 1300 cm$^{-1}$; $^1$H NMR=3.32 (m, 1H), 2.94 (m, 1H), 2.84 (m, 1H), 2.50 (m, 1H), 2.23 (m, 1H), 2.00 (m, 2H), $^{19}$F NMR=−101.6, 102.7 (2s, br, 1F), −116.7, −117.8 (2m, 1F), −169.2 (m, br, 1F); MS m/e=151 ([M−1]$^+$), Calc mass for $C_6H_6F_3O$=151.0371; Found: 151.0367.

In this case the only effect of lowering the ratio of the oxidizer/reactant as well as the temaerature, was lowering the conversion of the starting material from quantitative to 70%.

EXAMPLE 2

Epoxidation of 1,1,2-Trifluoro-1,7-Octadiene 160 mmols of tne oxidizing solution were made and cooled to −40° C. To this solution 9.7 a (60 mmol) of the olefin dissolyed in 30 ml $CH_2Cl_2$ were added also after cooling to −40° C. After 2 minutes the reaction was worked up as described above. After the distillation of the solvent the reaction mixture was distilled and the main fraction identified as 7,8-epoxy-1,1,2-trifluoro-1-octene with a bp=50–59° C./7 mm, yield 50%; $^1$H NMR=2.92 (m, br, 1H), 2.78 (t, J=4.2 Hz, 1H), 2.48 (m, 1H), 2.36 (m, 1H), 2.28 (m, 1H), 1.56 (m, 6H); $^{19}$F NMR=−105.9, −106.1, −106.4, −106.6 (4s, br, 1F), −124.9, −125.4, −125.5, −125.0 (4t, J=4.1 Hz, 1F), −174.6, −175.2 (dm, J=82.9 Hz, 1F); MS m/e=162 (M$^+$), 108 ([CF$_2$=CFCH$_2$CH$_2$−1]$^+$), 95 ([CF$_2$=CFCH$_2$]$^+$).

EXAMPLE 3

Epoxidation of 1,1,2-Trifluoro-1,9-Decadiene 65 mmols of the oxidizing solution were made. To this solution 5 g (26 mmol) of the olefin dissolved in 20 ml $CH_2Cl_2$ were added at −10° C. After 10 minutes the reaction was worked up as described above. After the distillation of the solvent the reaction mixture consisted of 19% starting material and 55% of 9,10-epoxy-1,1,2-trifluoro-1-decene; $^1$H NMR=2.95 (m, 1H), 2.78 (t, J=4 Hz, 1H), 2.46 (q, J$_1$=6 Hz, J$_2$=4 Hz, 1H), 1.3–2.4 ppm (m, 12H); $^{19}$F NMR=−106.5 (m, 1F), −125.7 (m, 1F), −175.1 (m, 1F); MS m/e=207 ([M−1]$^+$), Calc mass for $C_{10}H_{14}F_3O$=207.0997; Found: 207.1029; 95 ([CF$_2$=CFCH$_2$]$^+$).

EXAMPLE 4

Polymerization of 7,8-Epoxy-1,1,2-Trifluoro-1-Octene

Cooled 7,8-epoxy-1,1,2-trifluoro-1-octene (1.0 g) was placed in a dried flask. The temperature was raised to 25 to 30° C. and the neat substrate was stirred at this temperature for 10 days. The resulting viscous product was dissolved in an acetone (15 ml) and conc. HCl (0.5 ml) mixture with stirring. Water was added and the insoluble polymer laver was separated. This washing process was repeated for 2–3 times, the polymer isolated and was dried in which vacuum in desiccator. After drying, 100% yield of polymer was obtained with a weight average molecular weight of 32,200. F-19 NMR indicated that the polymerization was occurred on the epoxde exclusively, the CF$_2$=CF— was not involved in the polymerization. F-19 NMR (CDCl$_3$): −106.6 (dm, 1F), −125.6(tm, 1F), −174.8 (dm, 1F); H-1 NMR (CDCl$_3$): δ 3.50 (br, 3H), 2.30 (d, br, 2H), 1.50 (br, 6H).

EXAMPLE 5

Polymerization of 5,6-Epoxy-1,1,2-Trifluoro-1-Hexene

In a dried flask was charged 5,6-epoxy-1,1,2-trifluoro-1-hexene (0.912 g) and aluminum chloride initiator (13.5 mg). The polymerization proceeded at 85° C. for 24 hours. The resulting polymer was worked up as described in Example 4. 0.46 g of brown solid polymer was obtained with a Tg 24.7° C. This polymer has a weight average molecular weight of 10,900. The polymer structure was supported by its H-1 and F-19 NMR spectra.

EXPERIMENT 1

Preparation of 1,1,2-Trifluoro-1,6-Hexadiene

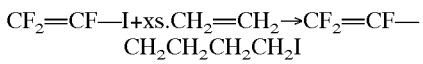

In a 1400 ml HC Shaker tube was charged iodotrifluoroethylene (71.3 g, 0.343 mole) and d-limonene (1.7 g). The tube was sealed, cooled and evacuated, and ethylene gas (240 g, 8.57 mole) was transferred into the tube. The tube was agitated and heated slowly to 200° C., then was kept at this temperature for 24 hrs. The product unloaded from the tube was purified by distillation. 61.0 g (67.4% yield) of 1,1,2-trifluoro-6-iodo-1-hexene was obtained as a clear licuid, Bp: 58° C./2.5 mm. $^1$H NMR (CDCl$_3$): δ 3.22 (m, 2H), 2.02 to 2.60 (m, 6H); F-19 NMR (CDCl$_3$): –103.5, –104.6 (2s, br, 1F), –114.7, –115.8 (2s, br, 1F), –164.1 (s, br, 1F).

1,1,2-Trifluoro-6-iodo-1-hexene (52.8 g, 0.2 mole) obtained from above was mixed with 10 M KOH aqueous solution (125 ml, 1.25 mole) and benzyldodecyl bis(2-hydroxypropyl)ammonium chloride (14.4 g, 60 wt. % aqueous solution, 0.02 mole) and was stirred for 24 hrs at room temperature. The too organic layer was then separated, washed with water, and distilled to give the title product, 20 g (73.5% yield), as a clear colorless liquid. Bp: 50° C./200 mm. $^1$H NMR (CDCl$_3$): δ 6.00 (m, 1H), 5.52 (m, 2H), 2.54 (m, 1H), 2.30 (m, 1H), 2.20 (m, 2H); F-19 NMR (CDCl$_3$): –100.8, –101.9 (2m, 1F), –115.4, –116.5 (2m, 1F), –161.8 (m, 1F).

EXPERIMENT 2

Preparation of 1,1,2-Trifluoro-1,8-Octadiene

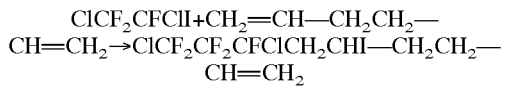

Sodium hydrosulfite (88%, 10 g, 0.05 mole), sodium bicarbonate (3.7 g, 0.05 mole) and acetonitrile (20 ml) were mixed at 40° C. with stirring. A solution of ClCF$_2$CFClI (56 g, 0.2 mole) and 1,5-hexadiene (33 g, 0.4 mole) was added. The reaction temperature was controlled at around 60° C. during the addition and was stirred for 1 hr at 60° C. after the addition was complete. The lower organic layer was separated and distilled to give the desired olefin product (35 g, 48% yield) as a clear licuid. Bp. 124–128° C./30 mm.

5-Iodo-7,8-dichloro-7,8,8-trifluoro-1-octene compound (36 g, 0.1 mole) from above in absolute ethanol (30 ml) was added slowly into a suspension of Zn (22 g, 0.3 mole)/EtOH (50 ml). An exothermic reaction was observed. The reaction mixture was refluxed for 1 hr after all the substrate was added. The mixture was poured into a dil. HCl/ice water mixture, and the bottom laver was separated, dried over MgSO$_4$. The fraction boiling at 88–90° C./15 mm was collected to give the desired product (14 g, 59% yield).

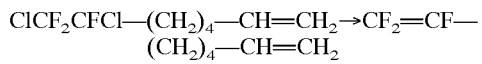

7,8-Dichloro-7,8,8-trifluoro-1-octene (23.7 g, 0.1 mole), Zn-dust (19.5 g, 0.3 mole) and DMSO solvent (50 ml) were mixed and was heated at 140–180° C. The distillate, which boiled at 120–140° C., was collected. The reaction was continued for about 4 hrs until no more product was distilled over. The distillate was washed with cold water, dried over Na$_2$S$_2$O$_4$ and distilled again to give the pure diolefin product (11 g, 66% yield) as a clear liquid. Bp. 118–120° C. $^1$H NMR (CDCl$_3$): 5.68 (m, 1H), 5.00 (d, 1H), 4.88 (s, 1H), 1.80–2.50 (m, 4H), 1.00–1.80 (m, 4H); F-19 NMR (CDCl$_3$): –105.5 (dd, 1F), –124.6 (dd, 1F), –174.7 (dm, 1F); IR: 1640 cm$^{-1}$, 1794 cm$^{-3}$.

CF$_2$=CF—(CH$_2$)$_6$—CH=CH$_2$ was synthesized similarly, Bp. 74–76° C./40 mm. $^1$H NMR (CDCl$_3$): 5.70 (m, 1H), 5.00 (dm, 1H), 4.82 (m, 1H), 1.80–2.50 (m, 4H), 0.80–1.80 (m, 8H); F-19 NMR (CDCl$_3$): –105.4 (dd, 1F), –124.5 (dd, 1F), –173.5 (dm, 1F); IR: 1640 cm$^{-1}$, 1795 cm$^{-1}$.

Although preferred embodiments of the invention have been described hereinabove, it is to be understood that there is no intention to limit the invention to the precise constructions herein disclosed, and it is to be further understood that the right is reserved to all changes coming within the scoce of the invention as defined by the appended claims.

We claim:

1. A polymer, comprising, units of the formula

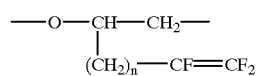

wherein n is an integer from 2 through 10.

2. The polymer as recited in claim 1 wherein said n is 2, 4 or 6.

3. The polymer as recited in claim 2 wherein said n is 4.

4. The polymer as recited in claim 1 that is a homopolymer.

5. The polymer as recited in claim 1 which is a copolymer with ethylene oxide and/or propylene oxide.

6. The polymer as recited in claim 5 which is a copolymer with ethylene oxide.

7. The polymer as recited in claim 5 which is a copolymer with propylene oxide.

8. The polymer as recited in claim 2 which is a copolymer with ethylene oxide and/or propylene oxide.

9. The polymer as recited in claim 8 which is a copolymer with ethylene oxide.

10. The polymer as recited in claim 8 which is a copolymer with propylene oxide.

* * * * *